US010544285B2

(12) United States Patent
Kobilka et al.

(10) Patent No.: US 10,544,285 B2
(45) Date of Patent: Jan. 28, 2020

(54) IMPACT RESISTANT CYCLIC PHOSPHAZENES

(71) Applicant: INTERNATIONAL BUSINESS MACHINES CORPORATION, Armonk, NY (US)

(72) Inventors: Brandon M. Kobilka, Tucson, AZ (US); Joseph Kuczynski, North Port, FL (US); Jacob T. Porter, Highland, NY (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 130 days.

(21) Appl. No.: 15/782,545

(22) Filed: Oct. 12, 2017

(65) Prior Publication Data

US 2019/0112452 A1 Apr. 18, 2019

(51) Int. Cl.

| C08F 212/08 | (2006.01) |
|---|---|
| C08F 236/06 | (2006.01) |
| C08F 230/02 | (2006.01) |
| C08F 212/14 | (2006.01) |
| C08F 220/56 | (2006.01) |
| C08F 8/40 | (2006.01) |
| C08K 5/5399 | (2006.01) |
| C08K 5/00 | (2006.01) |
| C07F 9/6581 | (2006.01) |

(52) U.S. Cl.
CPC ........ *C08K 5/5399* (2013.01); *C07F 9/65812* (2013.01); *C08F 8/40* (2013.01); *C08F 220/56* (2013.01); *C08K 5/0066* (2013.01)

(58) Field of Classification Search
CPC ........ C09D 5/06; C08F 212/08; C08F 236/06; C08F 230/02; C08F 212/14; C08F 220/56; C08F 8/40; C08F 2220/585
See application file for complete search history.

(56) References Cited

U.S. PATENT DOCUMENTS

| 2014/0150963 A1 | 6/2014 | He |
| 2015/0307707 A1 | 10/2015 | Jung et al. |
| 2016/0272812 A1 | 9/2016 | Zhou et al. |
| 2017/0029704 A1 | 2/2017 | Boday et al. |

FOREIGN PATENT DOCUMENTS

WO 2016174592 A1 11/2016

OTHER PUBLICATIONS

S. Rothemund et al., Preparation of Polyphosphazenes: A Tutorial Review, Chem. Soc. Rev., 2016, 45, 5200-5215.
(Continued)

*Primary Examiner* — Ling Siu Choi
*Assistant Examiner* — Thuy-Ai N Nguyen
(74) *Attorney, Agent, or Firm* — Patterson + Sheridan, LLP

(57) ABSTRACT

An impact-modified composition and a method of making an impact-modified composition are provided. In an embodiment, the method includes reacting a phosphazene material with an acrylamide material to form a functionalized phosphazene material; initiating a polymerization reaction on a reaction mixture comprising the functionalized phosphazene material and one or more monomers to form an impact-modified phosphazene material; and adding the an impact-modified phosphazene material to a polymeric material.

15 Claims, 3 Drawing Sheets

(56) References Cited

OTHER PUBLICATIONS

K. Krishnadevi et al., Development of halogen-free flame retardant phosphazene and rice husk ash incorporated benzoxazine blended epoxy composites for microelectronic applications, New J. Chem., 2015, 39, 6555-6567.

H. R. Allcock et al., Synthesis and Structure of Small-Molecule Cyclic Phosphazenes Bearing Ortho-Substituted Aryloxy and Phenoxy Substituents, Inorg. Chem., 1992, 31, 2734-2739.

IMPACT RESISTANT CYCLIC PHOSPHAZENES

FIELD OF THE DISCLOSURE

Materials and methods described herein relate to flame-retardant materials.

BACKGROUND

Plastic enclosures are ubiquitous in virtually all of today's electrical and electronic equipment (EEE). Although plastics can be readily injection molded into intricate, thin-walled structures, they also must meet important fire safety standards. Components in high-powered computers are highly concentrated heat sources that may result in rapid overheating and runaway thermal events. Electrical and electronic products are also subject to fire risks from electrical short circuits that can cause ignition within a product. Without the use of flame-retardants to mitigate ignition resistance, the potential for fire danger increases as the number of electronic products—and cables, wires and electronic chargers to power them—increases in households, offices and commercial buildings.

Examples of flame-retardants are phosphazenes and polyphosphazenes. Incorporating flame-retardants into the materials used in electrical and electronic components enables manufacturers to meet fire safety standards (Such as UL 94, *Standard for Tests for Flammability of Plastic Materials for Parts in Devices and Appliances*), while also ensuring a product meets key technical requirements such as weight, durability, flexibility, and impact resistance. As new and more sophisticated material technologies emerge, and requirements for fire resistant materials evolve, the flame-retardant itself must keep pace. Flame-retardant manufacturers will continue to innovate and develop effective and sustainable flame-retardants that meet new product demands for fire resistance, high performance and cost-effectiveness, and address environmental health and safety concerns.

Formulating plastic materials which meet not only flammability requirements, but key performance metrics (such as impact resistance), is an area of current research focus. Plastic manufacturers will often blend small molecule flame-retardants into the base thermoplastic to render it ignition resistant. However, there is always a trade off in physical properties. That is, by increasing the loading level of the flame-retardant (FR) to achieve a specific UL 94 rating, impact resistance is often degraded.

Moreover, plastics are typically derived from a finite and dwindling supply of petrochemicals, resulting in price fluctuations and supply chain instability. Replacing non-renewable petroleum-based polymers with polymers derived from renewable resources may be desirable. However, there may be limited alternatives to petroleum-based polymers in certain contexts. To illustrate, particular plastics performance standards may be specified by a standards body or by a regulatory agency. In some cases, alternatives to petroleum-based polymers may be limited as a result of challenges associated with satisfying particular plastics performance standards.

Thus, there is a need to compensate for degraded impact resistance while maintaining high levels of flame retardancy.

SUMMARY

Embodiments described herein relate to materials and methods of making flame-retardant polymers. To minimize impact resistance caused by addition of flame-retardants into the polymers, orthogonal functionality is incorporated into a polymeric flame-retardant such as polyphosphazene. The resulting material may be directly blended with a base polymer or covalently bound to the base polymer rendering it both flame-retardant and impact resistant.

According to an embodiment, a composition is provide. The composition includes a phosphazene represented by formula (I)

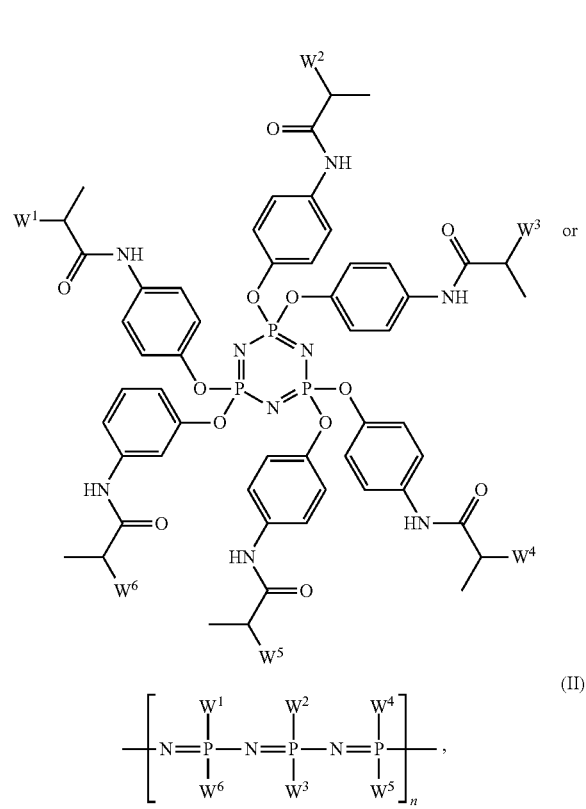

or a combination thereof,
wherein:
each of $W^1$, $W^2$, $W^3$, $W^4$, $W^5$, and $W^6$ is independently a vinyl polymer; and
n is about 1-200.

According to an embodiment, a method of forming an impact-modified phosphazene material is provided. The method includes reacting a phosphazene material with an acrylamide material to form a functionalized phosphazene material; and initiating a polymerization reaction on a reaction mixture comprising the functionalized phosphazene material and one or more monomers to form an impact-modified phosphazene material.

According to an embodiment, a method of forming an impact-modified phosphazene material is provided. The method includes reacting a phosphazene material with an acrylamide material to form a functionalized phosphazene material; initiating a polymerization reaction on a reaction mixture comprising the functionalized phosphazene material and one or more monomers to form an impact-modified phosphazene material; and adding the an impact-modified phosphazene material to a polymeric material.

One advantage of the present disclosure is the ability to impart flame-retardant characteristics to a copolymer by chemically binding phosphorus to a polymer chain. Another advantage of the present disclosure is the ability to add the flame-retardant copolymer to another polymeric material (e.g., a polylactic acid (PLA) homopolymer or a polymeric blend that includes a PLA polymer) in order to improve the impact resistance characteristics of the polymeric material without degrading the flame retardancy characteristics of the polymeric material.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

BRIEF DESCRIPTION OF THE SEVERAL VIEWS OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, for the disclosure may admit to other equally effective embodiments.

DETAILED DESCRIPTION

Figure 1:
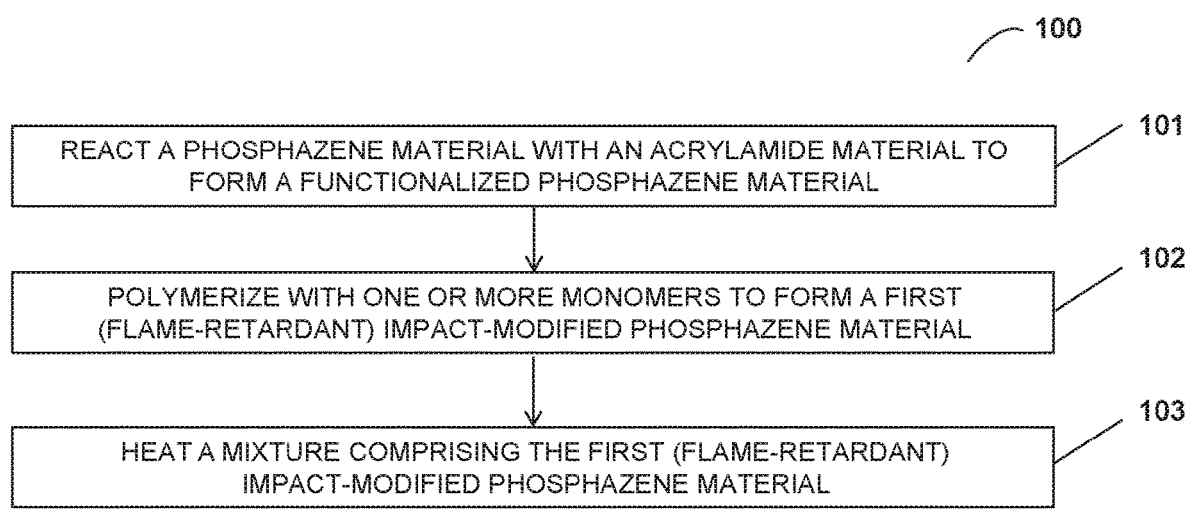
FIG. 1 shows a method of making an impact-modified phosphazene material according to an embodiment.

The present disclosure provides flame-retardant compositions and methods of making such compositions involving polyphosphazenes. More particularly, the present disclosure provides for compositions and methods for making phosphazenes that incorporate both flame-retardant and impact properties.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, and enantiomers of the represented compounds.

Unless otherwise noted, chemical reactions are performed at ambient conditions or under slight heating with no special atmosphere or head space, and may be performed using standard organic solvents to manage mix properties such as viscosity and flow index.

As used herein, "(flame-retardant) impact-modified phosphazene material" includes cyclic phosphazene materials with or without additional flame-retardant blocks, and polyphosphazene materials with or without additional flame-retardant blocks.

As used herein, "vinyl polymer" includes polymers resulting from polymerization of monomers having carbon-carbon double bonds. Such polymers may include residual unsaturation. Polymer includes anything that has monomers, including oligomers.

The present disclosure relates to production of impact-modified phosphazene materials for use as polymeric impact modifiers. In some cases, a polymeric material derived from renewable resources may have unacceptable impact resistance characteristics for use in various contexts (e.g., as enclosures surrounding computing devices). Illustrative, nonlimiting examples of polymeric materials derived from renewable resources include polylactic acid (PLA) homopolymers, polymeric blends that include a PLA polymer and a polycarbonate (PC) polymer (also referred to as a PLA/PC blend), polybutylene succinate (PBS) polymers, and polyhydroxy alkanoate (PHA) polymers. In order to improve the impact resistance characteristics of such polymeric materials, the (flame-retardant) impact-modified phosphazene materials of the present disclosure may be utilized as additives without degradation of flame retardancy characteristics that may be associated with other polymeric impact modifiers.

The (flame-retardant) impact-modified phosphazene materials include cyclic phosphazene materials and polyphosphazene materials. Phosphazenes are flame-retardant materials. The (flame-retardant) impact-modified phosphazene materials may contain additional flame-retardant blocks made of, for example, phosphorous-containing blocks or halogen-containing blocks. The phosphorous-containing blocks include an organophosphate material.

The (flame-retardant) impact-modified phosphazene materials of the present disclosure include, for example, methacrylate-butadiene-styrene (MBS) copolymers having a polymer chain that optionally include an organophosphate material. The present disclosure describes processes of producing such (flame-retardant) impact-modified phosphazene material by polymerizing, for example, a methacrylate monomer material, with other monomers, and optionally an organophosphate monomer. Other monomers include acrylic, styrenic, or other vinylic monomers. For example, the (flame-retardant) impact-modified phosphazene material may be produced by polymerizing a methacrylate monomer material, a butadiene monomer, a styrene monomer, and optionally an organophosphate monomer. The optional organophosphate monomer may include a phosphorus-containing acrylic monomer, a phosphorus-containing styrenic monomer, or a combination thereof (among other alternatives). Alternatively or additionally, an acrylic, styrenic, or other vinylic monomer having flame-retardant functionalities (e.g., phosphorus, halogens, etc.) may be suitable for use as a monomer to form a flame-retardant copolymer.

The additional flame-retardant characteristics of the (flame-retardant) impact-modified phosphazene materials of the present disclosure may allow the (flame-retardant) impact-modified phosphazene materials to be used as impact modifying additives without flame-retardant degradation that may be associated with other impact modifiers (e.g., MBS-based impact modifiers that do not include phosphorus). As an example, the (flame-retardant) impact-modified phosphazene materials of the present disclosure may have a first impact resistance value that is greater than a second impact resistance value of a PLA-based polymer (e.g., a PLA homopolymer or a PLA/PC blend, among other alternatives). As another example, the (flame-retardant) impact-modified phosphazene materials of the present disclosure may have a first flame retardancy value that is greater than a second flame retardancy value of an impact modifier that may improve impact resistance characteristics of a PLA-based polymer, but degrade flame-retardant characteristics of the PLA-based polymer.

In some cases, a (flame-retardant) impact-modified phosphazene material of the present disclosure may be used to form a polymeric blend with acceptable impact resistance properties that also satisfies a plastics flammability standard. As an illustrative, non-limiting example, the plastics flammability standard may be specified by Underwriters Laboratories® (referred to as "UL" herein), such as UL 94, entitled "Standard for Safety of Flammability of Plastic Materials for Parts in Devices and Appliances testing." The UL 94 standard defines various criteria that may be used to classify a particular plastic based on a degree of flame-retardancy. To illustrate, in order for a plastic to be assigned a "V-1" classification, UL 94 specifies that burning stops within 30 seconds on a vertical specimen and that drips of particles are allowed as long as the particles are not inflamed. In order for a plastic to be assigned a "V-0" classification, UL 94 specifies that burning stops within 10 seconds on a vertical specimen and that drips of particles are allowed as long as the particles are not inflamed. In some cases, testing may be conducted on a 5-inch×0.5-inch (12.7 cm×1.27 cm) specimen of a minimum approved thickness (according to the UL 94 standard). It will be appreciated that the UL 94 V-1/V-0 plastics flammability standards are for example purposes only. Alternative or additional plastics flammability standard(s) may be applicable in various contexts.

Thus, the present disclosure describes (flame-retardant) impact-modified phosphazene materials resulting from the phosphazene moieties, and in addition, the presence of an organophosphate material in the polymer chain. The flame-retardant characteristics of the (flame-retardant) impact-modified phosphazene materials of the present disclosure may allow the (flame-retardant) impact-modified phosphazene materials to be used as additives to improve impact resistance properties of a polymeric material (e.g., a PLA/PC blend) without degrading the ignition resistance properties of the polymeric material.

Common routes to poly(organo)phospazenes use the precursor poly(dichloro)-phosphazene [NPCl$_2$]$_n$ 1. One route to polyphosphazenes, as shown in Scheme 1, is a stepwise, mixed substitution reaction of different nucleophiles (for example, primary alcohols, R$^1$OH and R$^2$OH) proceeding through product 2, which is a poly(alkoxychloro)phosphazene. This reaction allows access to a broad range of copolymers such as phosphazene 3, which is a poly(alkoxy) phosphazene. Another mixed substitution reaction is a stepwise addition of different primary amines (for example, primary amines R$^1$NH$_2$ and R$^2$NH$_2$) proceeding through product 4, which is a poly(chloroalkylamino)phosphazene, to access a range of copolymers such as phosphazene 5. These mixed substitution reactions allow for fine-tuning of the polymer's properties.

Scheme 1:

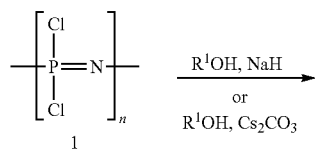

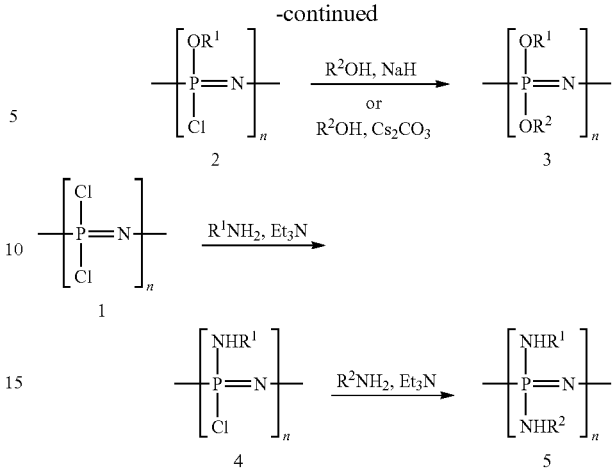

The compounds described above have flame-retardant properties typical of poly(phosphazenes) without further modification, but further functionality can be incorporated as described below to increase their flame-retardant properties.

While all available sites of the cyclic phosphazenes, as described below, can be modified to incorporate desired functionality (for example, compounds 203, 301, and 401), it is also contemplated that only a few sites may be modified using stoichiometric reaction conditions to limit the number of functional groups. Thus, the mix of substituents can be changed and controlled using stoichiometry. You can starve this reaction of methacrylate to get PBS-only sub stituents, and you can starve the reaction of reagents altogether to get unsubstituted protected phenols.

In general, starting from cyclotriphosphazene, hexa(m-ethacrylamidophenyl)cyclotriphosphazene is derived. Hexa (methacrylamidophenyl)cyclotriphosphazene can then be functionalized with MBS (methacrylate-butadiene-styrene) and an FR polymer-forming monomer, such as phosphorus-containing acrylates or 4-(diphenylphosphino)styrene, both of which are commercially available and/or are known in the prior art for imparting flame-retardant characteristics. These are exemplary and non-limiting examples, and any acrylic, styrenic, or otherwise vinylic monomer known for containing flame-quenching functionalities (phosphorus, halogens, etc.) and known to polymerize via, for example, radical polymerization are suitable substitutes. The (flame-retardant) impact-modified cyclic phosphazene or (flame-retardant) impact-modified polyphosphazene is then blended into a matrix of the desired commercial bio-renewable polymers such as PLA, PLA/PC, or other suitable formulations. The as-described compounds do not have to include additional flame-retardant moieties and can be made to only include the impact modifier, all of which is discussed below. It does not need to be included due to the flame-retardant properties that the phosphazene moiety offers.

According to an embodiment, and referring to Scheme 2, hexachlorocyclotriphosphazene ("HCTP") 200 may be transformed to hexa(methacrylamidophenyl)cyclotriphosphazene ("HMTP") 203 by reaction with p-methacrylamidophenoxide (generated in situ). p-Methacrylamidophenol is used in excess. Instead of using the p-methacrylamidophenol, analogous reactions can also be performed with methacrylatephenols(4-hydroxyphenyl methacrylate) or their sodium salts to give a methacrylate analogous to the methacrylamide.

Scheme 2:

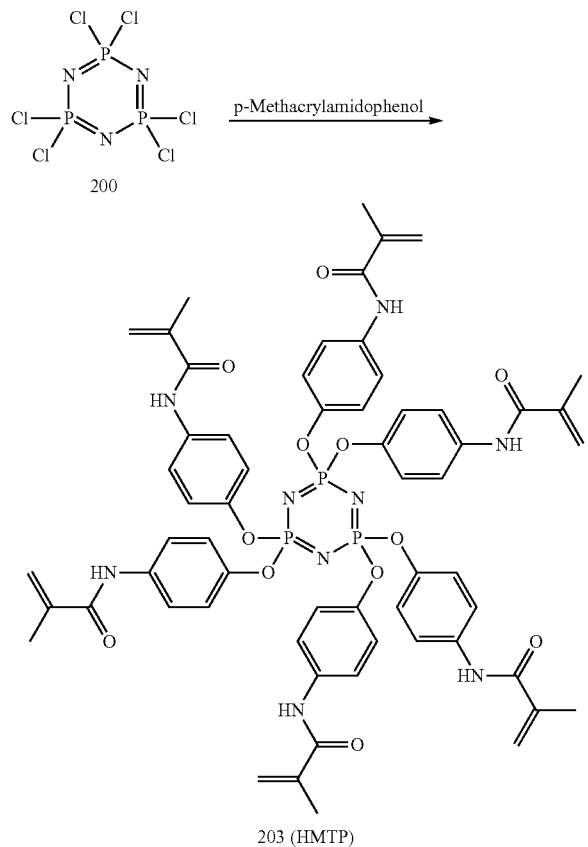

203 (HMTP)

HMTP 203 is a cyclotriphosphazene with mixed methacrylatephenol and methacrylamidophenol substituents at the phosphate locations. HMTP 203 may have all methacrylatephenol substituents, all methacrylamidophenol substituents, or any mixture thereof according to the stoichiometry employed in Scheme 2.

The synthesis of HMTP 203, with only methacrylamidophenol substituents, may be performed by the following process. To a stirred solution of molecule 200 (1.0 eq.) and p-methyacrylamidophenol in anhydrous THF or dioxane at 40° C. under argon, is added a base which may include potassium carbonate, cesium carbonate, or sodium hydride. The base is added portion-wise and the reaction mixture is stirred for about 15 minutes, followed by heating to 60° C. or reflux for a period of 24 hours. Upon completion, the reaction is mixed with water, and the layers separated. The aqueous layer is extracted with diethyl ether or ethyl acetate several times. The organic layers are combined and washed with ammonium chloride and/or brine and dried over magnesium sulfate. The solvents may be removed in vacuo and the crude product may be purified by recrystallization or column chromatography.

Methacrylatephenol may be mixed with, or substituted for, p-methacrylamidophenol to make the HMTP 203 with methacrylatephenol substituents. It should be further noted that other acrylatephenols and/or acrylamidophenols may be used in Scheme 2 to yield analogous HMTP-substituted cyclotriphosphazenes. Moreover, any material that can undergo polymerization is contemplated, such as styrene-based materials, butadiene-styrene-based materials, or other vinyl materials may be used. Furthermore, vinyl-terminated oligomers, xylenols, and preformed polymer blocks can be used. Other compounds of interest include dimethyl amino styrenes, p-methoxy styrenes, p-methyl styrenes, alpha-methyl styrenes, isoprenes, vinyl naphthalenes, p-chlorostyrenes, vinyl pyridines, diphenyl ethylenes, alkyl methacrylates, propiolactones, propylene sulfides, vinylidene cyanides, and alpha-cyanoacrylates.

Schemes 3-5, as illustrated below, detail the copolymerization of HMTP with a mixture of styrene, butadiene, and optionally nominal amounts of a phosphorus-containing acrylate via Reversible Addition-Fragmentation chain Transfer (RAFT) polymerization to give poly(methacrylate-co-butadiene-co-styrene)-functionalized HMTP (MBS-HMTP). The additional flame-retardant group may not be necessary in all cases, but provides an additional synergistic flame retardancy when used. Common radical polymerization techniques using thermal initiators, UV initiators, controlled radical polymerization, and the like are suitable.

According to an embodiment, and referring to Scheme 3, a poly(methacrylate-co-butadiene-co-styrene)-functionalized HMTP (MBS-HMTP-1, 301) is formed by a polymerization of HMTP with styrene and butadiene by one of the known radical polymerization techniques listed above. PBS is a polybutadiene-styrene, where x is about 1-12,500, and y is about 1-12,500, preferably, x is about 100-12,500, and y is about 100-12,500.

Scheme 3:

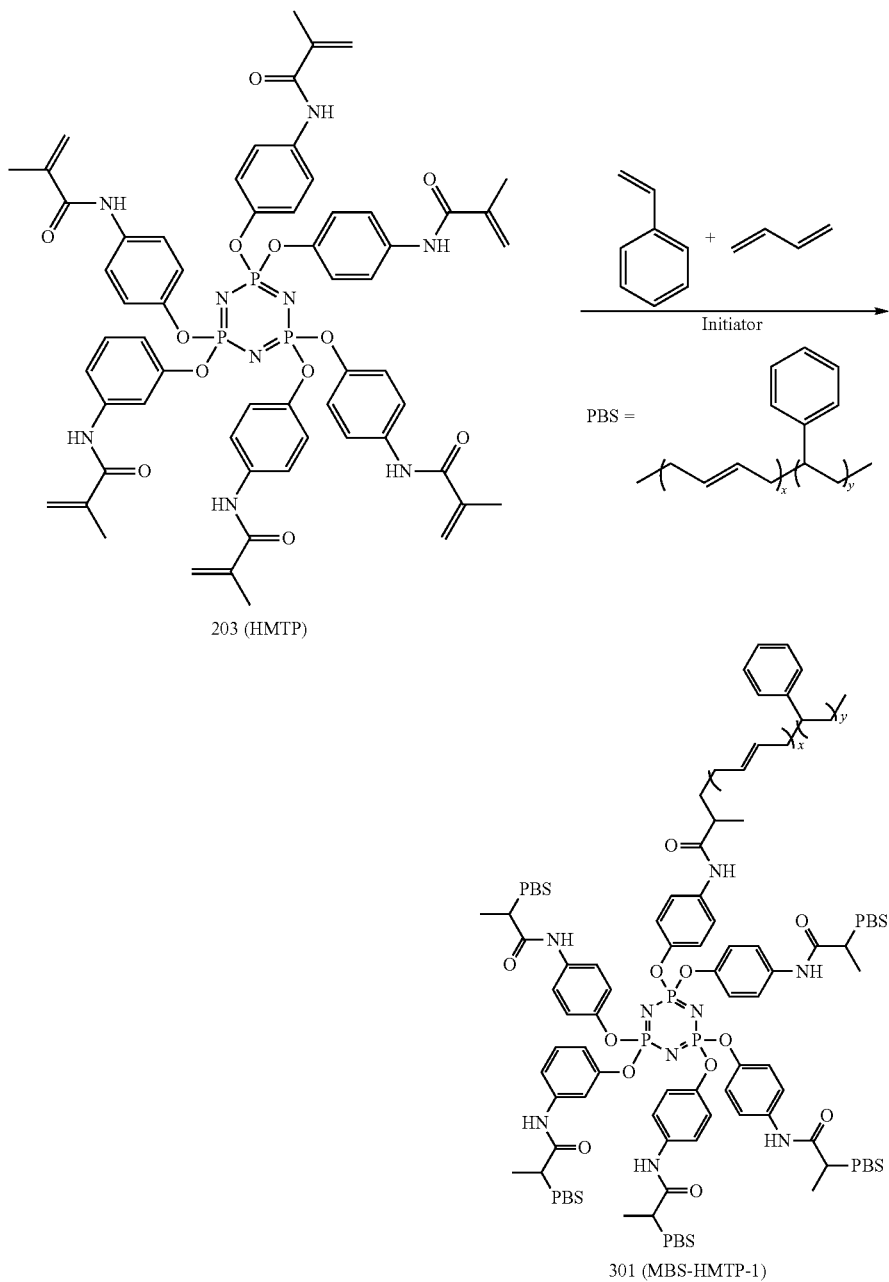

As used herein, "PBS*" means polybutadiene-styrene with an additional flame-retardant moiety (i.e., an organophosphate). As used herein, "PBS" means polybutadiene-styrene without an additional flame-retardant moiety (i.e., an organophosphate).

As used herein, "Ph" means a phenyl ring.

The reaction may be performed by the following process. To a bulk quantity or a stirred solution of HMTP 203 is added an initiator such as 2,2'-Azobis(2-methylpropionitrile) (AIBN), 4,4'-azobis(4-cyanovaleric acid) (ACVA), or benzoyl peroxide (0.05-0.5 mol %), a RAFT agent such as 2-Cyano-2-propyl benzodithioate or 4-Cyano-4-[(dodecylsulfanylthiocarbonyl)sulfanyl]pentanoic acid (0.05-0.5 mol %), excess styrene, and excess polybutadiene in an anhydrous solvent such as benzene degassed by three freeze-pump-thaw cycles. The mixture is heated with stirring at about 60° C. for about 4 to about 24 hours, and may be precipitated into a non-solvent such as hexane or methanol and purified using techniques such as re-precipitation or Soxhlet extraction.

Other initiators that can be used for the processes described herein include azo initiators such as 4,4'-Azobis(4-cyanovaleric acid), 1,1'-Azobis(cyclohexanecarbonitrile), Azobisisobutyronitrile 12 wt. % in acetone, 2,2'-Azobis(2-methylpropionamidine) dihydrochloride granular, and 2,2'-Azobis(2-methylpropionitrile), and 2,2'-Azobis(2-methylpropionitrile). Such azo initiators are commercially available from Sigma Aldrich.

Other peroxides that can be used for the processes described herein include di-tert-butyl peroxide (DTBP), tent-Butyl hydroperoxide, tent-Butyl peracetate, Cumene hydroperoxide, 2,5-Di(tert-butylperoxy)-2,5-dimethyl-3-hexyne, 2,5-Di(tert-butylperoxy)-2,5-dimethyl-3-hexyne, Dicumyl peroxide, 2,5-Bis(tert-butylperoxy)-2,5-dimethyl-hexane, 2,4-Pentanedione peroxide, 1,1-Bis(tert-butylperoxy)-3,3,5-trimethylcyclohexane, 1,1-Bis(tert-butylperoxy)cyclohexane, 1,1-Bis(tert-amylperoxy)cyclohexane, Benzoyl peroxide, 2-Butanone peroxide, 2-Butanone peroxide, tent-Butyl peroxide, Lauroyl peroxide, tent-Butyl peroxybenzoate, and tert-Butylperoxy 2-ethylhexyl carbonate. These agents may be in solution with other agents or combined with solvents stabilizers, plasticizers, calcium carbonate and/or silica.

RAFT agents may be selected according to monomer class, transfer constant, hydrolytic stability, among other factors. Common RAFT agents include trithiocarbonates, dithiocarbamates, dithiobenzoates, Switchable RAFT agents, and Macro-RAFT agents.

Other RAFT agents that can be used for the processes described herein include specifically, trithiocarbonates: such as 3,5-Bis(2-dodecylthiocarbonothioylthio-1-oxopropoxy) benzoic acid, 3-Butenyl 2-(dodecylthiocarbonothioylthio)-2-methylpropionate, 2-(2-Carboxyethyl sulfanylthiocarbonyl sulfanyl)propionic acid, 4-((((2-Carboxyethyl)thio)carbonothioyl)thio)-4-cyanopentanoic acid, 2-Cyanobutan-2-yl 4-chloro-3,5-dimethyl-1H-pyrazole-1-carbodithioate, 2-Cyanobutanyl-2-yl 3,5-dimethyl-1H-pyrazole-1-carbodithioate, 4-Cyano-4-[(dodecylsulfanylthiocarbonyl)sulfanyl] pentanoic acid, 4-Cyano-4-[(dodecylsulfanylthiocarbonyl)sulfanyl]pentanol, Cyanomethyl (3,5-Dimethyl-1H-pyrazole)-carbodithioate, Cyanomethyl dodecyl trithiocarbonate, Cyanomethyl [3-(trimethoxysilyl)propyl] trithiocarbonate, 2-Cyano-2-propyl dodecyl trithiocarbonate, S,S-Dibenzyl trithiocarbonate, 2-(Dodecylthiocarbonothioylthio)-2-methylpropionic acid, 2-(Dodecylthiocarbonothioylthio)-2-methylpropionic acid 3-azido-1-propanol ester, 2-(Dodecylthiocarbonothioylthio)-2-methylpropionic acid N-hydroxysuccinimide ester, 2-(Dodecylthiocarbonothioylthio)-2-methylpropionic acid pentafluorophenyl ester, 2-(Dodecylthiocarbonothioylthio)propionic acid, Methyl 2-(dodecylthiocarbonothioylthio)-2-methylpropionate, Pentaerythritol tetraki s [2-(dodecylthiocarbonothioylthio)-2-methylpropionate], Phthalimidomethyl butyl trithiocarbonate, Poly(acrylic acid), DDMAT terminated average $M_n$ 10,000, PDI≤1.1, Poly(ethylene glycol) bis[2-(dodecylthiocarbonothioylthio)-2-methylpropionate] average $M_n$ 10,800, Poly(ethylene glycol) methyl ether 4-cyano-4-[(dodecyl sulfanylthiocarbonyl)sulfanyl]pentanoate average $M_n$ 10,000, Poly(ethylene glycol) methyl ether (4-cyano-4-pentanoate dodecyl trithiocarbonate) average $M_n$ 5,400, Poly(ethylene glycol) methyl ether (4-cyano-4-pentanoate dodecyl trithiocarbonate) average $M_n$ 2,400, Poly(ethylene glycol) methyl ether (4-cyano-4-pentanoate dodecyl trithiocarbonate) average $M_n$ 1,400, Poly(ethylene glycol) methyl ether 2-(dodecylthiocarbonothioylthio)-2-methylpropionate average $M_n$ 5,000, Poly(ethylene glycol) methyl ether 2-(dodecylthiocarbonothioylthio)-2-methylpropionate average $M_n$ 1,100, Poly(ethylene glycol) methyl ether (2-methyl-2-propionic acid dodecyl trithiocarbonate) average $M_n$ 10,000, Poly(L-lactide) 4-cyano-4-[(dodecylsulfanylthiocarbonyl)sulfanyl] pentonate, Poly(L-lactide) 4-cyano-4-[(dodecylsulfanylthiocarbonyl)sulfanyl]pentonate $M_n$ 10,000, PDI≤1.2, Poly(D, L-lactide), 4-cyano-4-[(dodecyl sulfanylthiocarbonyl) sulfanyl]pentonate terminated average $M_n$ 5000, PDI≤1.5, Polystyrene, DDMAT terminated average $M_n$ 10,000, PDI≤1.1, and 1,1,1-Tris [(dodecylthiocarbonothioylthio)-2-methylpropionate] ethane; Dithiocarbamates: such as Benzyl 1H-pyrrole-1-carbodithioate, Cyanomethyl diphenylcarbamodithioate, Cyanomethyl methyl(phenyl) carbamodithioate, Cyanomethyl methyl(4-pyridyl) carbamodithioate, 2-Cyanopropan-2-yl N-methyl-N-(pyridin-4-yl)carbamodithioate, Methyl 2-[methyl(4-pyridinyl)carbamothioylthio]propionate, and 1-Succinimidyl-4-cyano-4-[N-methyl-N-(4-pyridyl)carbamothioylthio]pentanoate; Dithiobenzoates: such as Benzyl benzodithioate, Cyanomethyl benzodithioate, 4-Cyano-4-(phenylcarbonothioylthio)pentanoic acid, 4-Cyano-4-(phenylcarbonothioylthio)pentanic acid N-succinimidyl ester, 2-Cyano-2-propyl benzodithioate, 2-Cyano-2-propyl 4-cyanobenzodithioate, Ethyl 2-(4-methoxyphenylcarbonothioylthio)acetate, Ethyl 2-methyl-2-(phenylthiocarbonylthio)propionate, Ethyl 2-(phenylcarbonothioylthio)-2-phenylacetate, Ethyl 2-(phenylcarbonothioylthio)propionate, 1-(Methoxycarbonyl)ethyl benzodithioate, 2-(4-Methoxyphenylcarbonothioylthio)ethanoic acid, 2-Nitro-5-(2-propynyloxy)benzyl 4-cyano-4-(phenylcarbonothioylthio)pentanoate, 2-(Phenylcarbonothioylthio)propanoic acid, and 2-Phenyl-2-propyl benzodithioate; Switchable RAFT agents: such as Cyanomethyl methyl(4-pyridyl)carbamodithioate, 2-Cyanopropan-2-yl N-methyl-N-(pyridin-4-yl)carbamodithioate, Methyl 2-[methyl(4-pyridinyl)carbamothioylthio]propionate, and 1-Succinimidyl-4-cyano-4-[N-methyl-N-(4-pyridyl)carbamothioylthio]pentanoate; and Macro-RAFT agents: such as Poly(acrylic acid), DDMAT terminated average Mn 10,000, PDI≤1.1, Poly(tert-butyl acrylate), DDMAT terminated, azide terminated average Mn 8,500, PDI≤1.2, Poly(tert-butyl acrylate), DDMAT terminated average Mn 7,000, Poly(N,N-dimethylacrylamide), DDMAT terminated average Mn 10,000, PDI≤1.1, Poly (ethylene glycol) bis[2-(dodecylthiocarbonothioylthio)-2-methylpropionate] average Mn 10,800, Poly(ethylene glycol) 4-cyano-4-(phenylcarbonothioylthio)pentanoate average Mn 10,000, Poly(ethylene glycol) 4-cyano-4-(phenylcarbonothioylthio)pentanoate average Mn 2,000, Poly (ethylene glycol) methyl ether 4-cyano-4-[(dodecylsulfanylthiocarbonyl)sulfanyl]pentanoate average Mn 10,000, Poly (ethylene glycol) methyl ether (4-cyano-4-pentanoate dodecyl trithiocarbonate) average Mn 5,400, Poly(ethylene glycol) methyl ether (4-cyano-4-pentanoate dodecyl trithiocarbonate) average Mn 2,400, Poly(ethylene glycol) methyl ether (4-cyano-4-pentanoate dodecyl trithiocarbonate) average Mn 1,400, Poly(ethylene glycol) methyl ether 2-(dodecylthiocarbonothioylthio)-2-methylpropionate average Mn 5,000, Poly(ethylene glycol) methyl ether 2-(dodecylthiocarbonothioylthio)-2-methylpropionate average Mn 1,100, Poly(ethylene glycol) methyl ether (2-methyl-2-propionic acid dodecyl trithiocarbonate) average Mn 10,000, Poly (hydroxyethyl methacrylate), DDMAT terminated average Mn 7,000, PDI<1.2, Poly(D,L-lactide), 4-cyano-4-[(dodecylsulfanylthiocarbonyl)sulfanyl]pentonate terminated average Mn 20,000, PDI <1.4, Poly(D,L-lactide), 4-cyano-4-[(dodecylsulfanylthiocarbonyl)sulfanyl]pentonate terminated average Mn 10,000, PDI<1.4, Polystyrene, DDMAT terminated average Mn 10,000, PDI≤1.1, and Polystyrene, DDMAT terminated average Mn 5,000, PDI<1.1. Such RAFT agents are commercially available from Sigma Aldrich.

According to an embodiment, and referring to Scheme 4A, a poly(methacrylate-co-butadiene-co-styrene)-functionalized HMTP (MBS-HMTP-2, 401) is formed by a polymerization of HMTP 203 with styrene, butadiene, and 2-((diphenylphosphoryl)oxy)ethyl methacrylate 400 by one of the known radical polymerization techniques listed above. PBS² is a polybutadiene-styrene, where x is about 1-12,500, y is about 1-12,500, and z is about 1-12,500, preferably, x is about 100-12,500, and y is about 100-12,500, and z is about 100-12,500.

The synthesis of MBS-HMTP-2, 401, may be performed in an analogous procedure to the synthesis of MBS-HMTP-1, 301. Other RAFT agents, azo initiators and peroxides described herein can be used for the process.

In an embodiment, and as shown in Scheme 4B, the phosphorous-functionalized acrylate monomer 400 is syn- Scheme 4A:

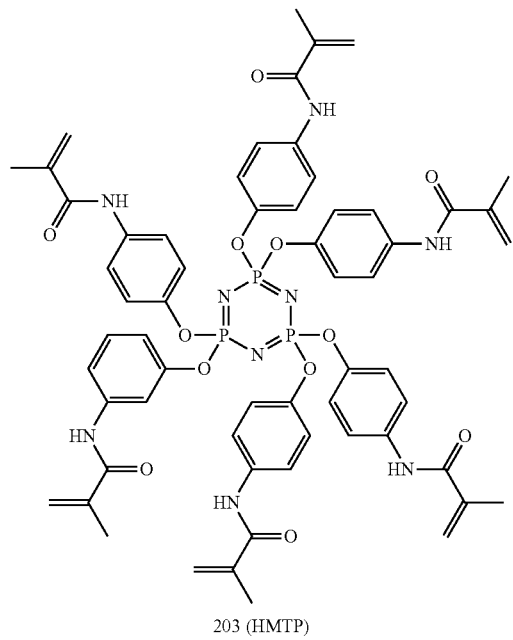

203 (HMTP)

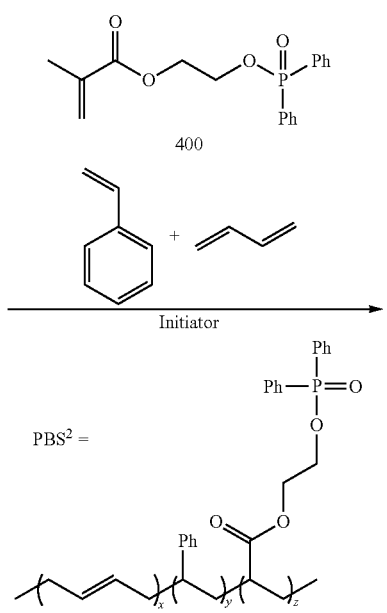

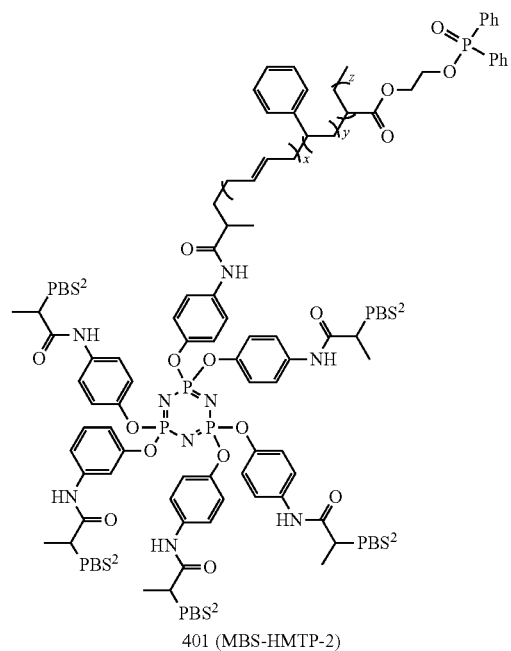

401 (MBS-HMTP-2)

thesized from 2-hydroxyethyl methacrylate 402, from Sigma-Aldrich. The synthesis uses a phosphorous reactant such as diphenylphosphinic chloride 403A or diphenylphosphoryl chloride 403B with trimethylamine (Et₃N), 4-and dimethylaminopyridine (DMAP) as catalyst, in dichloromethane (DCM) to provide monomer 400. Triethylamine (1.2 equiv.) and N,N-dimethylaminopyridine (DMAP) (3.0 mol %) is added to a stirred solution of 2-hydroxymethyacrylate (1.0 equiv.) in 150 mL of DCM, under argon, and cooled to 0° C. A solution of diphenylphosphoryl chloride or diphenylphosphinic chloride in DCM (1.1 equiv.) is added dropwise at 0° C. Upon completion of the addition, the reaction mixture is allowed stir for 1 hour at 0° C., is warmed to room temperature and stirred for 16 hours. The reaction mixture is subsequently washed about twice with water, followed by 1N HCl, about three additional washes of water, and brine. The organic layer is dried over anhydrous sodium sulfate, filtered, and the solvents removed in vacuo. The product may be purified by fractional distillation.

Scheme 4B:

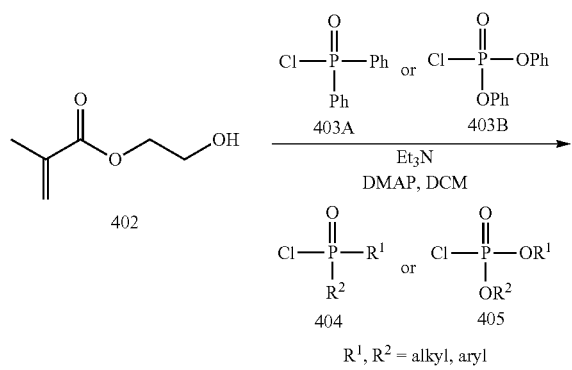

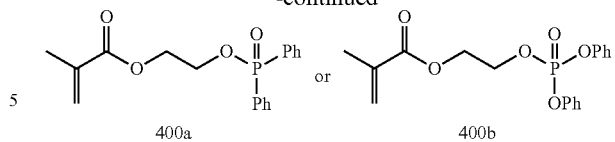

Other phosphorous-based molecules can be used for the synthesis of the phosphorous-functionalized acrylate monomers. As shown in Scheme 4B, such phosphorous-based molecules include phosphorous reactants 404 and 405 where each of $R^1$ and $R^2$ is independently alkyl or aryl. These alkyl and aryl groups may be branched or unbranched, substituted or unsubstituted. This allows for an expanded class of molecules similar to MBS-HMTP-2 (401) to be synthesized, wherein one or more of the phenyl groups is replaced by $R^1$ and/or $R^2$. It is contemplated that any suitable phosphorous reactant may be utilized to prepare the flame-retardant and impact resistant phosphazenes.

According to an embodiment, and referring to Scheme 5A, a poly(methacrylate-co-butadiene-co-styrene)-functionalized HMTP (MBS-HMTP-3, 501) is formed by a polymerization of HMTP 203 with styrene, butadiene, and 4-(diphenylphosphino)styrene 500 by one of the known radical polymerization techniques listed above. 4-(diphenylphosphino)styrene is commercially available from Sigma-Aldrich. PBS³ is a polybutadiene-styrene, where x is about 1-12,500, y is about 1-12,500, and z is about 1-12,500, preferably, x is about 100-12,500, and y is about 100-12,500, and z is about 100-12,500.

Scheme 5A:

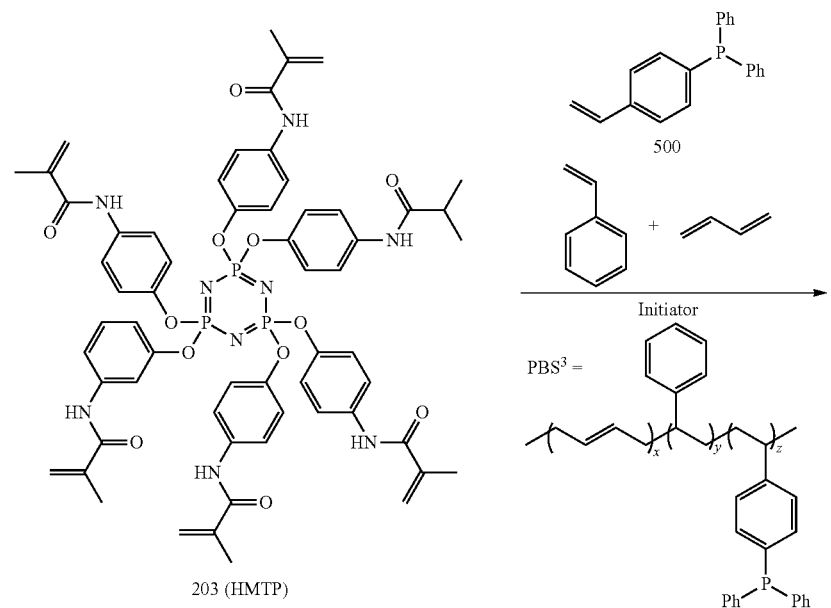

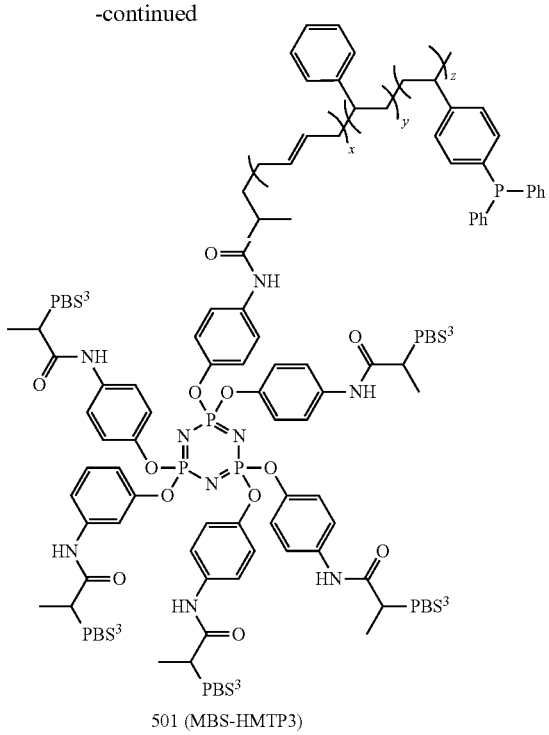

501 (MBS-HMTP3)

The synthesis of MBS-HMTP-3, 501, may be performed in an analogous procedure to the synthesis of MBS-HMTP-1, 301. Other RAFT agents, azo initiators and peroxides described herein can be used for the process.

In an embodiment, and as shown in Scheme 5B, diphenyl styrenyl phosphine 500 can be substituted with other phosphorous-functionalized styrene monomers, including styrenyl phosphine oxide 502, styrenyl phosphonate 503, styrenyl phosphate 504, and styrenyl phosphinate 505. In each of compounds 502-505, each of $R^1$ and $R^2$ is independently alkyl or aryl. These alkyl and aryl groups may be branched or unbranched, substituted or unsubstituted. Schemes 5C, 5D, and 5E illustrate the syntheses of 502-505 from commercially available starting materials and reagents.

Scheme 5B:

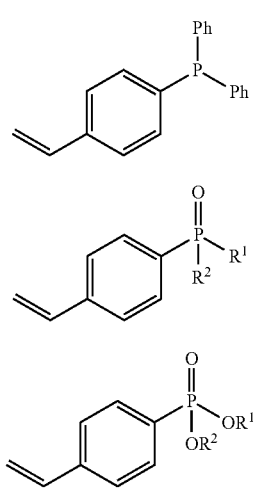

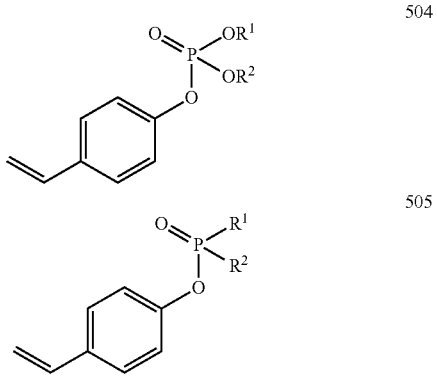

$R^1, R^2$ = alkyl, aryl

In an embodiment, and as shown in Scheme 5C, a styrenyl phosphine oxide 502 ($R^1$, $R^2$=phenyl) as a non-limiting example is synthesized from a styrenyl phosphine 500 ($R^1$, $R^2$=phenyl) by reaction with oxone, $H_2O$, methanol (MeOH), and 1,1-dichloroethane ($C_2H_4Cl_2$). p-Styryldiphenyl phosphine (1.0 equiv.) and 1,2-dichloroethane (0.2 M) is added to a round-bottom flask. Saturated aqueous solutions of oxone (2.0 equiv.) and methanol (20% v/v) is added to the reaction flask and the mixture is stirred for 2 h. The reaction mixture and a large excess of water is added to a separatory funnel, and the two layers separated. The organic layer is retained and the solvent removed in vacuo. The sticky solid is washed with cyclohexane and then filtered.

Scheme 5C:

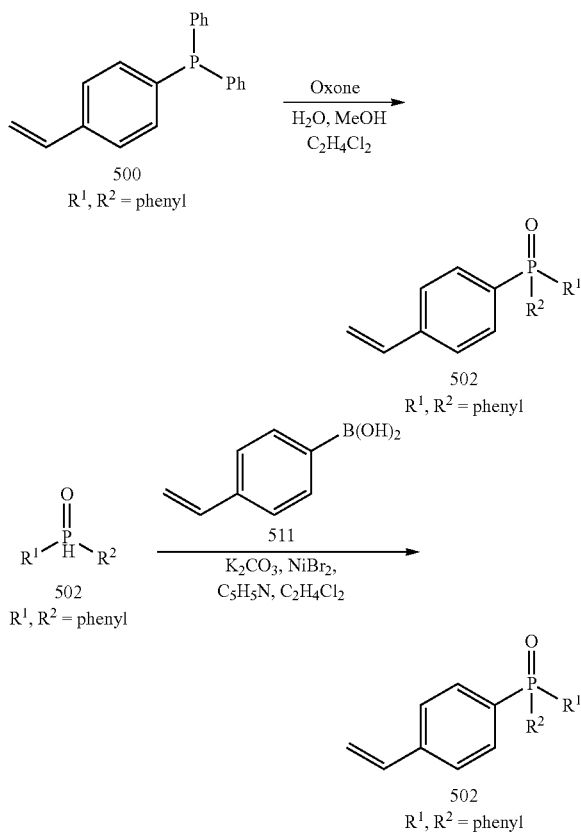

(1.0 equiv) (which may be synthesized by stirring a DCM solution of 4-vinylphenol with triflic anhydride in the presence of pyridine at 0° C.), diphenyl phosphonate 506 (1.2 equiv), N,N-diisopropylethylamine (1.5 equiv), Tris(dibenzylideneacetone)dipalladium(0) (Pd$_2$(dba)$_3$) (5 mol %), and 1,3-bis(diphenylphosphino)propane (Ph$_2$P(CH$_2$)$_3$PPh$_2$) (5 mol %) in toluene (PhMe), under argon, is stirred at 110° C. for 40 h. The mixture is cooled to room temperature and filtered through celite. The solution is concentrated, and purified by column chromatography on silica gel. Standard procedures for solvent removal can then be performed to provide the styrenyl phosphonate 503 (R$^1$, R$^2$=phenyl).

Scheme 5D:

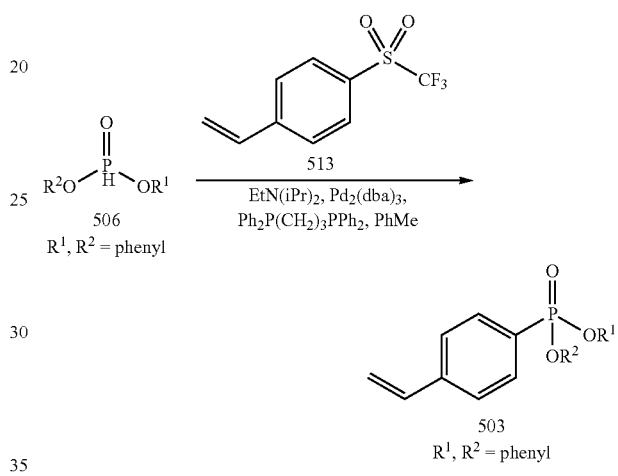

Alternatively, the reaction as shown in Scheme 5C may be accomplished by the following procedure. Diphenylphosphine oxide 510 (1 equiv.), 4-styryl boronic acid 511 (1.5 equiv.), NiBr$_2$ (1 mol %) and pyridine (0.15 mmol) or 2,2-bipyridyl (0.075 mmol), and K$_2$CO$_3$ (2 equiv) is dissolved in 1,2-dichloroethane and stirred at 100° C. for 24 h under an argon atmosphere (under air for 2,2-bipyridyl). The resulting mixture may be purified by, for example, silica gel chromatography using a mixture of petroleum ether and ethyl acetate as eluent. Standard procedures for solvent removal can then be performed to provide the styrenyl phosphine oxide 502 (R$^1$, R$^2$=phenyl).

In another embodiment, and as shown in Scheme 5D, a styrenyl phosphonate 503 as a non-limiting example is synthesized from a phosphoric ester 506 (R$^1$, R$^2$=phenyl) by the following procedure. A solution of p-styryl triflate 513

In another embodiment, and as shown in Scheme 5E, styrenyl phosphates 504 can be synthesized from 4-vinylphenol 507 using phosphoric esters 506 (R$^1$, R$^2$=alkyl, aryl), and lithium tert-butoxide (LiOtBu), in a solution of carbon tetrachloride (CCl$_4$). As a non-limiting example, phosphoric ester 506 (R$^1$, R$^2$=phenyl) is used as a starting material. A reaction vessel, such as a Schlenk tube, is charged with diphenylphosphine oxide (2.0 equiv.), 4-vinylphenol (1.0 equiv.), lithium tert-butoxide (2.0 equiv.) and CHCl$_3$ (1 M), under an inert atmosphere. The mixture is stirred at room temperature for 30 minutes, and the volatiles removed in vacuo. The product may be purified from the crude mixture by, for example, being passed through a pad or column of silica gel using petroleum ether/ethyl acetate (5:1) as the eluent. Standard procedures for solvent removal can then be performed to provide the styrenyl phosphate 504 (R$^1$, R$^2$=phenyl).

Scheme 5E:

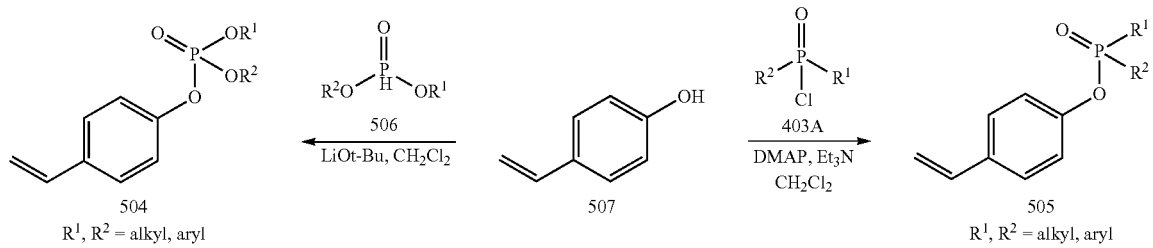

Styrenyl phosphinates 505 ($R^1$, $R^2$=Ph) may be synthesized from 4-vinylphenol 507 using chlorides 403A ($R^1$, $R^2$=alkyl, aryl) and DMAP in a solution of dichloromethane. As a non-limiting example, chloride 403A ($R^1$, $R^2$=phenyl) is used as a starting material. Triethylamine (1.2 equiv.) and N,N-dimethylaminopyridine (DMAP) (3.0 mol %) is added to a stirred solution of 4-vinylphenol (1.0 equiv.) in 150 mL of dichloromethane ($CH_2Cl_2$, DCM), under argon, and cooled to 0° C. A solution of diphenyl chlorophosphate (1.1 equiv.) in DCM is added dropwise at 0° C. Upon completion of the addition, the reaction mixture is allowed stir for 1 hour at 0° C., and is warmed to room temperature and stirred for 16 hours. The reaction mixture is subsequently washed about twice with water, followed by 1N HCl, about three additional washes of water, and brine. The organic layer is dried over anhydrous sodium sulfate, filtered, and the solvents removed in vacuo. The product may be purified by fractional distillation to provide the styrenyl phosphinate 505 ($R^1$, $R^2$=phenyl).

According to an embodiment, the ring-opened form of the cyclic phosphazene may be used for the impact-modified phosphazene material (with or without an additional flame-retardant moiety) as shown in Scheme 6. MBS-HMTP (601) is used as a representative example for any MBS-HMTP with additional flame-retardant moieties ($PBS^x$) or without additional flame-retardant moieties (PBS) contemplated herein. Upon heating, the cyclic phosphazene will ring open to afford polyphosphazenes 603. This reaction is accomplished by heating the resulting polymer to about 250° C. under an inert environment or reduced pressure.

Scheme 6:

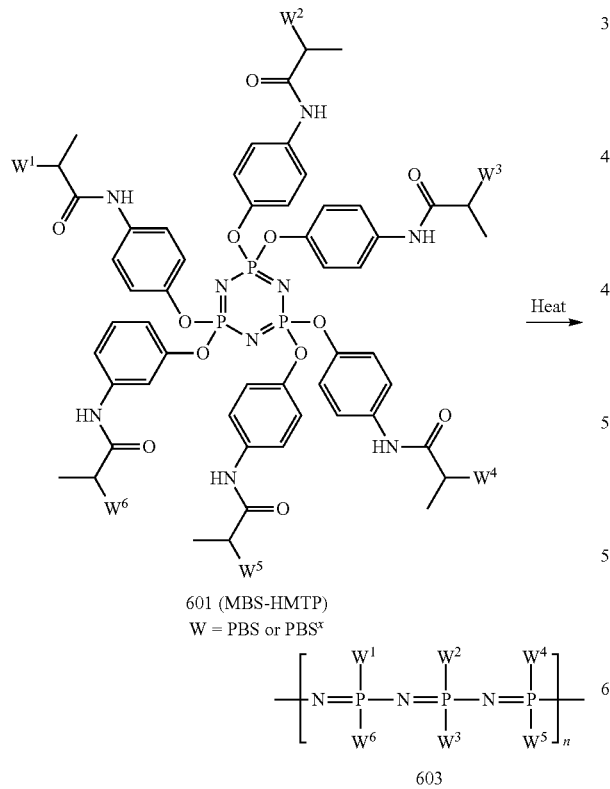

601 (MBS-HMTP)
W = PBS or $PBS^x$

603

One skilled in the art would appreciate that W groups ($W^1$, $W^2$, $W^3$, $W^4$, $W^5$, and $W^6$) may be the same or different within the phosphazene material. For example, the polymer chains can be grown from a mixture of monomers, i.e., co-monomers reacting from the same mixture at the about the same time. Y can also vary by growing the polymer chains prior to synthesizing the cyclophosphazene ring, and using a mixture of different phenols with varying side chains.

Phosphazenes 603 made according to Scheme 6, from starting material 601 as a representative example, include compounds wherein n is about 1-200. Each of $W^1$, $W^2$, $W^3$, $W^4$, $W^5$ and $W^6$ can be a same or different impact modifier. $PBS^x$ is a polybutadiene-styrene with an additional flame-retardant moiety (i.e., $PBS^2$ and $PBS^3$), where x is about 1-12,500, y is about 1-12,500, and z is about 1-12,500, preferably, x is about 100-12,500, and y is about 100-12,500, and z is about 100-12,500. PBS is a polybutadiene-styrene, where x is about 1-12,500, and y is about 1-12,500, preferably, x is about 100-12,500, and y is about 100-12,500.

In an embodiment, a composition is provided. The composition includes a phosphazene represented by formula (I)

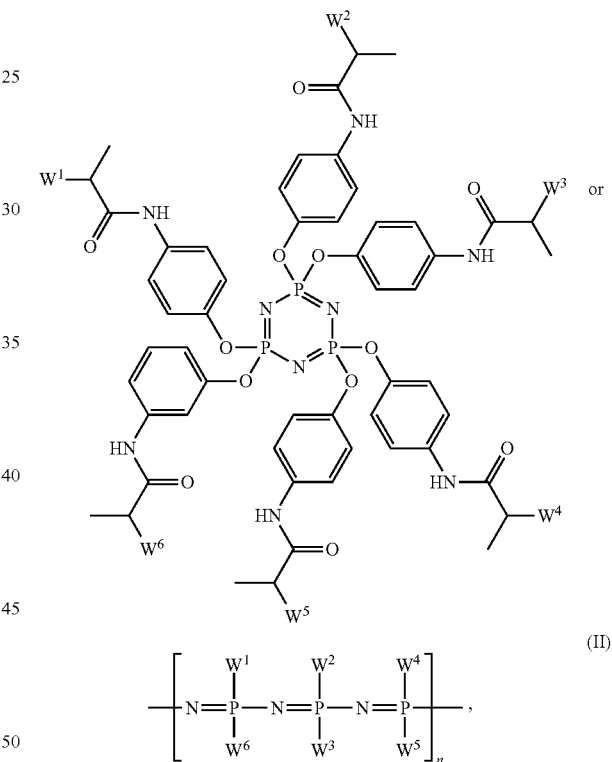

or a combination thereof,
wherein:
each of $W^1$, $W^2$, $W^3$, $W^4$, $W^5$, and $W^6$ is independently a vinyl polymer; and
n is about 1-200.

The impact-modified phosphazene materials of the present disclosure include, for example, methacrylate-butadiene-styrene (MBS) copolymers having a polymer chain that optionally includes an organophosphate material. Such materials can be made by polymerizing, for example, a methacrylate monomer material, with other monomers, and optionally an organophosphate monomer. Other monomers include acrylic, styrenic, or other vinylic monomers. For example, the (flame-retardant) impact-modified phosphazene material may be produced by polymerizing a methacrylate monomer material, a butadiene monomer, a styrene monomer, and optionally an organophosphate monomer. The optional organophosphate monomer may include a phosphorus-containing acrylic monomer, a phosphorus-containing styrenic monomer, or a combination thereof (among other alternatives). Alternatively or additionally, an acrylic, styrenic, or vinylic monomer having flame retardant functionalities (e.g., phosphorus, halogens, etc.) may be suitable for use as a monomer to form a flame-retardant copolymer.

In some embodiments, the vinyl polymer comprises an acrylate monomer, acrylamide monomer, styrenic monomer, other vinylic monomer, or combination thereof. The vinyl polymer may also be a product of a reaction comprising an acrylate monomer, acrylamide monomer, styrenic monomer, or other vinylic monomer, or combination thereof.

Examples of such monomers include methacrylates, a methacrylamides, butadienes, styrenes, acrylonitriles, isocyanates, butyl acrylates, ethylenes, and propylenedienes, or other materials with olefins. Examples of oligomers based on these monomers include methacrylate-butadiene styrene (MB S) material, poly(butadiene styrene) material (PBS), methacrylamide-butadiene styrene material, acrylonitrile-styrene-butyl acrylate (ASA) material, acrylonitrile-butadiene-styrene (ABS) material, methacrylate-acrylonitrile-butadiene-styrene (MABS) material, methacrylate-butadiene (MB) material, and acrylonitrile-ethylene-propylenediene-styrene (AES) material. Other monomers of interest include vinyl-terminated oligomers, xylenols, dimethyl amino styrenes, p-methoxy styrenes, p-methyl styrenes, alpha-methyl styrenes, isoprenes, vinyl naphthalenes, p-chlorostyrenes, vinyl pyridines, diphenyl ethylenes, alkyl methacrylates, propiolactones, propylene sulfides, vinylidene cyanides, and alpha-cyanoacrylates. Preformed polymer blocks may also be used.

In some embodiments, each of $W^1$, $W^2$, $W^3$, $W^4$, $W^5$, and $W^6$ is independently

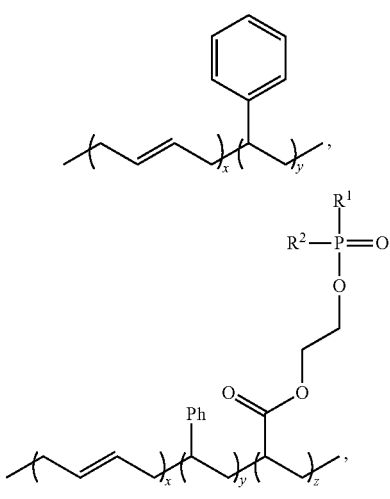

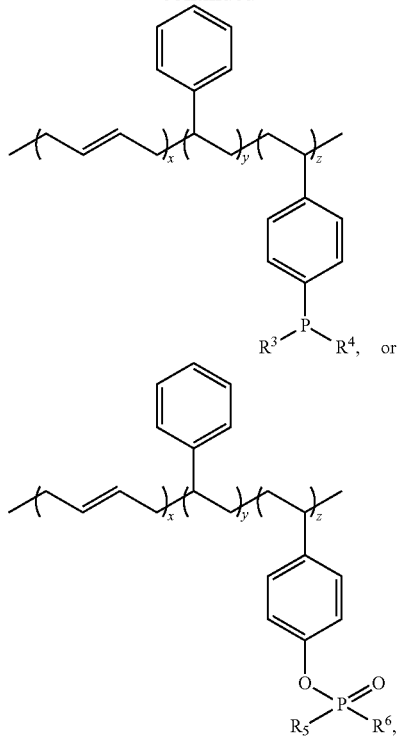

wherein:
each of $R^1$, $R^2$, $R^3$, $R^4$, $R^5$, and $R^6$ is independently unsubstituted hydrocarbyl, substituted hydrocarbyl, unsubstituted aryl, substituted aryl, unsubstituted alkoxy, substituted alkoxy, unsubstituted aryloxy, or substituted aryloxy, and
x is about 1-12,500;
y is about 1-12,500; and
z is about 1-12,500.

In some embodiments, the vinyl polymer is 1 to 40 wt % of the composition.

In some embodiments, and as discussed below, the composition further includes a polymeric material.

In an embodiment and as shown in FIG. 1, a method 100 of making an impact-modified phosphazene material is provided. The method includes reacting a phosphazene material with an acrylamide material to form a functionalized phosphazene material at operation 101; and initiating a polymerization reaction on a reaction mixture comprising a functionalized phosphazene material and one or more monomers to form a (flame-retardant) impact-modified phosphazene material at operation 102. The polymerization reaction of operation 102, may, for example, comprise adding an ultraviolet initiator, a thermal initiator, or a radical polymerization initiator. At operation 103, a mixture comprising the (flame-retardant) impact-modified phosphazene material may heated.

In addition, operation 102 includes one or more monomers. These monomers include acrylate monomer material, acrylamide monomer material, styrenic monomer material, vinylic monomer material, or a combination thereof. Examples of such monomers include methacrylates, methacrylamides, butadienes, styrenes, acrylonitriles, isocyanates, butyl acrylates, ethylenes, and propylenedienes. Examples of oligomers based on these monomers include methacrylate-butadiene styrene (MBS) material, poly(butadiene styrene) material (PBS), methacrylamide-butadiene styrene material, acrylonitrile-styrene-butyl acrylate (ASA) material, acrylonitrile-butadiene-styrene (ABS) material, methacrylate-acrylonitrile-butadiene-styrene (MABS) material, methacrylate-butadiene (MB) material, and acrylonitrile-ethylene-propylenediene-styrene (AES) material. Other monomers of interest include vinyl-terminated oligomers, xylenols, dimethyl amino styrenes, p-methoxy styrenes, p-methyl styrenes, alpha-methyl styrenes, isoprenes, vinyl naphthalenes, p-chlorostyrenes, vinyl pyridines, diphenyl ethylenes, alkyl methacrylates, propiolactones, propylene sulfides, vinylidene cyanides, and alpha-cyanoacrylates. Preformed polymer blocks may also be used.

Moreover, the reaction mixture may optionally comprise a phosphorous-containing monomer (i.e., an organophosphate). Such organophosphates may further increase the flame-retardancy of the phosphazene material. The optional organophosphate monomer may include a phosphorus-containing acrylic monomer, a phosphorus-containing styrenic monomer, or a combination thereof (among other alternatives). Alternatively or additionally, an acrylic, styrenic, or vinylic monomer having flame-retardant functionalities (e.g., phosphorus, halogens, etc.) may be suitable for use as a monomer to form a flame-retardant copolymer. Examples of the phosphorous-containing monomer include:

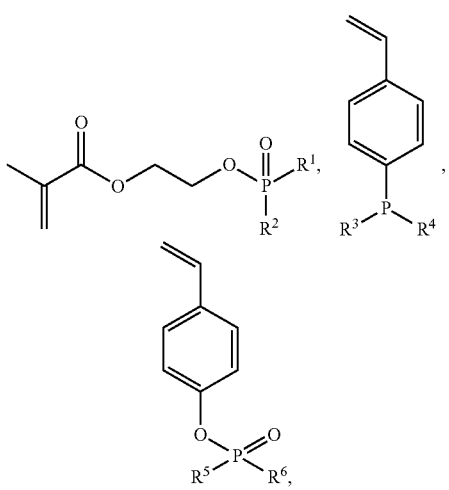

or combinations thereof,
wherein:
each of $R^1$, $R^2$, $R^3$, $R^4$, $R^5$, and $R^6$ is independently unsubstituted hydrocarbyl, substituted hydrocarbyl, unsubstituted aryl, substituted aryl, unsubstituted alkoxy, substituted alkoxy, unsubstituted aryloxy, or substituted aryloxy.

In an embodiment, the impact-modified phosphazene material may be represented by formula (I)

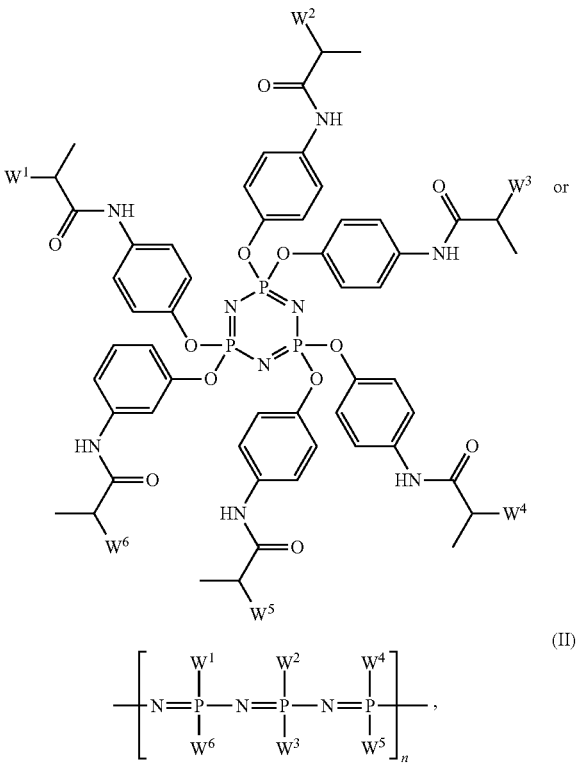

or a combination thereof,
wherein:
each of $W^1$, $W^2$, $W^3$, $W^4$, $W^5$, and $W^6$ is independently a vinyl polymer; and
n is about 1-200.

The phosphazenes are made, for example, according to Schemes 3-6 as described herein.

Figure 2:
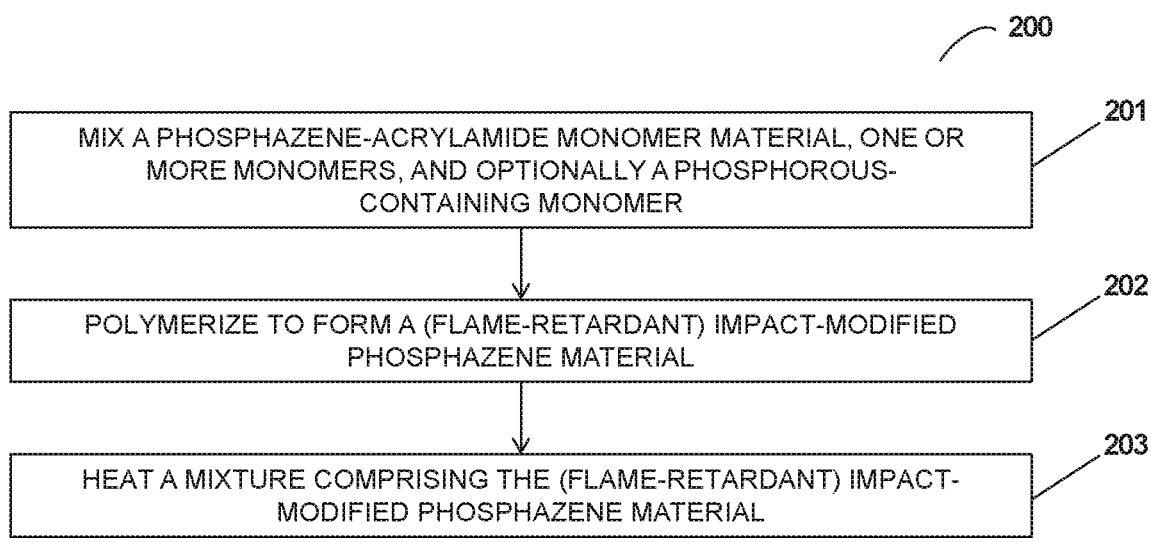
FIG. 2 shows a method of making an impact-modified phosphazene material according to an embodiment.

In an embodiment and as shown in FIG. 2, a method 200 of making an impact-modified polymeric material is provided. The method 200 includes mixing a phosphazene-acrylamide monomer material, one or more monomers, and optionally a phosphorous-containing monomer to form a mixture at operation 201. At operation 202, a polymerization reaction may be used to form a (flame-retardant) impact-modified phosphazene material. In operation 202, the mixture may further comprise a phosphorous-containing monomer, which can include any phosphorous-containing material described herein. Moreover, in operation 201, the polymerization includes adding an ultraviolet initiator, a thermal initiator, or a radical polymerization initiator. At operation 201, the phosphazene-acrylamide monomer may be derived from a reaction comprising a phosphazene material with an acrylamide material. At operation 203, a mixture comprising the (flame-retardant) impact-modified phosphazene is heated.

Compositions with Polymeric Materials

Figure 3:
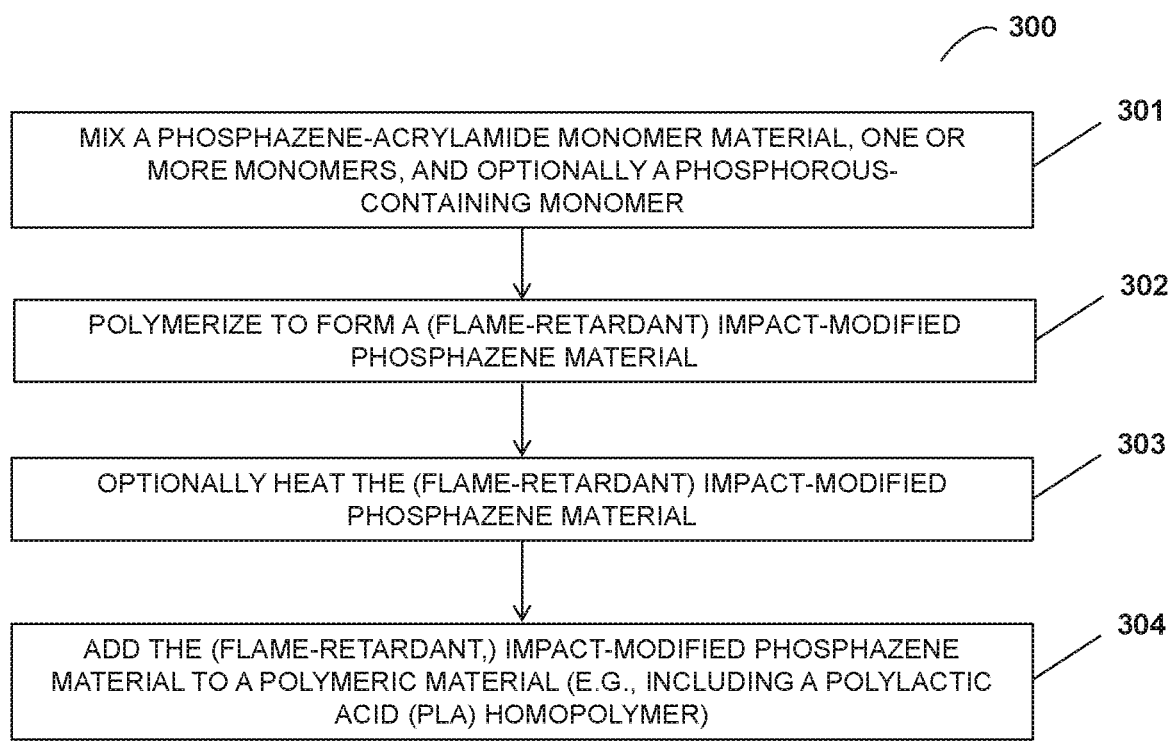
FIG. 3 shows a method of improving impact resistance of a polymeric material by adding an impact-modified phosphazene material.

In an embodiment, the compositions further include a polymeric material. Moreover, in an embodiment, a method of making (flame-retardant) impact-modified phosphazene materials for use as polymeric impact modifiers is described. In certain cases, a polymer or polymer blend may have unacceptable impact resistance characteristics for use in various contexts (e.g., as enclosures surrounding computing devices). Illustrative, non-limiting examples of polymers and polymer blends that may be derived from renewable resources include, for example, polylactic acid (PLA) homopolymers, polymeric blends that include a PLA polymer and a polycarbonate (PC) polymer (also referred to as a PLA/PC blend), polybutylene succinate polymers, and polyhydroxy alkanoate (PHA) polymers. In order to improve the impact resistance characteristics of such polymeric materials, the (flame-retardant) impact-modified phosphazene materials of the present disclosure may be utilized as additives without degradation of flame retardancy characteristics that may be associated with other polymeric impact modifiers. In a preferred embodiment, the impact-modified cyclic phosphazenes with or without flame-retardant blocks and the impact-modified polyphosphazenes with or without flame-retardant blocks may be compounded with a polymer or polymer blend desired for various applications, for example for bio-based formulations, including PLA-formulations, as shown in FIG. 3.

In an embodiment, a flame-retardant, impact-modified cyclic phosphazene and a flame-retardant impact-modified polyphosphazene may include at least a flame-retardant block (i.e., the phosphorous-containing acrylate blocks, and the phosphorous-containing styrenyl blocks) illustrated in Schemes 4A, 5A, and 6 (W=PBS$^x$). These flame-retardant, impact-modified materials may be used to improve an impact resistance value of another polymeric material. As an illustrative, non-limiting example, the flame-retardant, impact-modified materials may have a first impact resistance value that is greater than a second impact resistance value of a PLA homopolymer (or a PLA/PC blend, among other alternatives). As such, the addition of the flame-retardant, impact-modified materials of Schemes 4A, 5A, and 6 (W=PBS$^x$) to a PLA homopolymer or a PLA/PC blend may result in a polymeric blend with improved impact resistance characteristics.

In another embodiment, and as shown in Schemes 3 and 6 (W=PBS) an impact-modified cyclic phosphazene and an impact-modified polyphosphazene does not include a flame-retardant block (i.e., the phosphorous-containing acrylate blocks, and the phosphorous-containing styrenyl blocks). Synthesizing the impact-modified phosphazene materials without flame-retardant blocks, may be chosen, for example, when no additional flame-retardant properties are desired due to the phosphazene having flame-retardant properties. These impact-modified materials may be used to improve an impact resistance value of another polymeric material. As an illustrative, non-limiting example, the impact-modified materials may have a first impact resistance value that is greater than a second impact resistance value of a PLA homopolymer (or a PLA/PC blend, among other alternatives). As such, the addition of the impact-modified materials of Schemes 3 and 6 (W=PBS) to a PLA homopolymer or a PLA/PC blend may result in a polymeric blend with improved impact resistance characteristics.

The flame-retardant, impact-modified phosphazene materials illustrated by any of Schemes 4A, 5A, and 6 (W=PBS$^x$) may have a first flame retardancy value that is greater than a second flame retardancy value of an impact-modified phosphazene that does not include phosphorus illustrated by Schemes 3 and 6 (W=PBS).

An amount of phosphorus in the flame-retardant, impact-modified phosphazene materials may be adjusted such that, when used as a polymeric impact modifier, the (flame-retardant) impact-modified phosphazene material may improve impact resistance characteristics without flame retardancy degradation. In the embodiments illustrated in Schemes 4A, 5A, and 6, the amount of phosphorus in the flame-retardant, impact-modified phosphazene materials of Schemes 4A, 5A, and 6 may be varied by adjusting the stoichiometry of the reactant materials such that more/less of the phosphorus-containing acrylic monomer is polymerized.

As described further herein with respect to FIG. 3, the impact-modified cyclic phosphazenes with or without flame-retardant blocks and the impact-modified polyphosphazenes with or without flame-retardant blocks (collectively, "(flame-retardant) impact-modified phosphazene") may be used to form a polymeric blend that satisfies a plastics flammability standard and that provides acceptable impact resistance characteristics. Illustrative, non-limiting examples of plastics flammability standards include the UL 94 V-1 classification and the UL 94 V-0 classification. In order to be assigned the V-1 classification, UL 94 specifies that burning stops within 30 seconds on a vertical specimen and that drips of particles are allowed as long as the particles are not inflamed. In this case, a weight percentage of the (flame-retardant) impact-modified phosphazene material that is used as an additive may be adjusted such that the resulting polymeric blend satisfies the UL 94 V-1 standard. As another example, in order to be assigned the V-0 classification, UL 94 specifies that burning stops within 10 seconds on a vertical specimen and that drips of particles are allowed as long as the particles are not inflamed. In this case, a weight percentage of the (flame-retardant) impact-modified phosphazene material that is used as an additive may be adjusted such that the resulting polymeric blend satisfies the UL 94 V-0 standard.

With regard to the impact resistance characteristics, in some cases, the polymeric blend that includes the (flame-retardant) impact-modified phosphazene material may be compared to a "benchmark" polymeric material, such as a polymeric blend of a polycarbonate polymer and an acrylonitrile butadiene styrene (ABS) polymer (also referred to as a PC/ABS blend). In some cases, a polymeric blend that includes the (flame-retardant) impact-modified phosphazene material may be considered to have "acceptable" impact resistance properties when the polymeric blend satisfies an impact resistance threshold that is based on the benchmark polymeric material. To illustrate, an impact resistance characteristic may include a notched izod impact strength. In the case of a PC/ABS blend, the notched izod impact strength may be about 8-12 ft-lb/inch. In this case, the impact resistance properties of the polymeric blend that includes the (flame-retardant) impact-modified phosphazene material may be represented as a percentage of the notched izod impact strength of the PC/ABS blend. In a particular embodiment, to be considered acceptable, a notched izod impact strength of a polymeric blend that includes the (flame-retardant) impact-modified phosphazene material may be not less than about 50 percent of the notched impact strength of the PC/ABS blend, such as not less than about 60 percent, not less than about 70 percent, not less than about 80 percent, or not less than about 90 percent.

FIG. 3 is a flow diagram of a particular embodiment of a method 300 of improving impact resistance of a polymeric material by adding a polymeric impact modifier that includes a (flame-retardant) impact-modified phosphazene materials. The method 300 includes mixing a phosphazene-acrylamide monomer material, one or more monomers, and optionally a phosphorous-containing (organophosphate) monomer at operation 301. At operation 302, a polymerization reaction on the mixture forms a (flame-retardant) impact-modified phosphazene material. As an example, the organophosphate monomer may include a phosphorus-containing acrylic monomer, and a phosphorus-containing styrenic monomer, and a phosphorous-containing vinylic material. The method 300 optionally includes heating the (flame-retardant) impact-modified phosphazene material at operation 303. As shown in Scheme 6, heating the cyclic phosphazene provides the ring-opened phosphazene. Depending on application, both cyclic and ring-opened (acyclic) forms may be used in operation 304.

The process 300 includes adding the (flame-retardant) impact-modified phosphazene material (cyclic, acyclic, or a combination thereof) as an impact modifier to a polymeric material, at operation 304. Addition of the (flame-retardant) impact-modified phosphazene material may improve impact resistance of a polymeric material (while not degrading flame retardance). As an example, one or more of the (flame-retardant) impact-modified phosphazene material(s) described herein may be added to a polymeric material, preferably bio-based polymeric materials, such as a PLA-based polymer, including PLA-PC blends.

In a particular embodiment, an amount of the (flame-retardant) impact-modified phosphazene material that is added as an impact modifier may vary depending on the particular polymeric material, a desired impact resistance value, desired flame retardancy characteristics, or a combination thereof. In some cases, it may be desirable to increase an amount of one or more renewable polymeric materials in a polymeric blend. As an illustrative, non-limiting example, a PLA/PC blend that contains about 40 weight percent PLA and about 60 weight percent PC may be more desirable than a PLA/PC blend that contains about 30 weight percent PLA and about 70 weight percent PC (due to the increased amount of the renewable PLA content). In a particular embodiment, an amount of the (flame-retardant) impact-modified phosphazene material that is added to a polymeric material as an impact modifier in order to provide acceptable impact resistance properties and acceptable flame retardance properties may be in a range of about 1 weight percent to about 20 weight percent, such as in a range of about 5 weight percent to about 15 weight percent, in a range of about 8 weight percent to about 12 weight percent, or in a range of about 9 weight percent to about 11 weight percent.

It will be appreciated that other flame-retardant materials, such as different phosphorus-based flame-retardant blocks or halogen-based flame-retardant blocks may also be added to the polymeric blend to provide acceptable flame retardancy characteristics. As an example, for the polymeric blend to be classified as V-1/V-0 under UL 94, the phosphorus-based flame-retardant small molecule additives may represent about 10 weight percent to about 15 weight percent of the polymer matrix. Thus, while the flame retardancy characteristics of the (flame-retardant) impact-modified phosphazene materials of the present disclosure may allow them to be used as impact modifiers without flame retardancy degradation of the polymeric blend, additional material(s) may be utilized in order to satisfy a particular plastics flammability standard.

In the particular embodiment illustrated in FIG. 3, a process of forming a (flame-retardant) impact-modified phosphazene material is identified as operations 301-303, while a process of adding the (flame-retardant) impact-modified phosphazene material as an impact modifier is identified as operation 304. It will be appreciated that the operations shown in FIG. 3 are for illustrative purposes only and that the operations may be performed by a single entity or by multiple entities. As an example, one entity may form the (flame-retardant) impact-modified phosphazene material, while another entity may form a polymeric blend by adding the (flame-retardant) impact-modified phosphazene material as an impact modifier to another polymeric material.

Thus, FIG. 3 illustrates various operations associated with improving impact resistance properties of a polymeric material (e.g., a PLA homopolymer or a PLA/PC polymeric blend) via the addition of one or more of the (flame-retardant) impact-modified phosphazene material of the present disclosure. As an example, the (flame-retardant) impact-modified phosphazene material of the present disclosure may have a first impact resistance value that is greater than a second impact resistance value of a PLA-based polymer (e.g., a PLA homopolymer or a PLA/PC blend, among other alternatives). As another example, the (flame-retardant) impact-modified phosphazene material of the present disclosure may have a first flame retardance value that is greater than a second flame retardance value of an impact modifier that may improve impact resistance characteristics of a PLA-based polymer but degrade flame-retardant characteristics of the PLA-based polymer.

The (flame-retardant) impact-modified phosphazene material may be added to the polymeric material by any technique known in the art, including twin-screw compounding, extrusion (i.e., reactive extrusion, hot melt extrusion), and solvent coating/casting. Such techniques, among others, are known to those skilled in the art. Those skilled in the art will also appreciate that adjustment of the chain lengths of the MBS blocks, as well as adjustment of the monomer types and ratios affect the resulting polymer properties (i.e., modulating the melting temperature and glass transition temperature). Additionally, additives such as plasticizers and processing additives may be added to aid in adding the impact-modified phosphazene material to the polymeric material.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A composition comprising: a phosphazene represented by formula

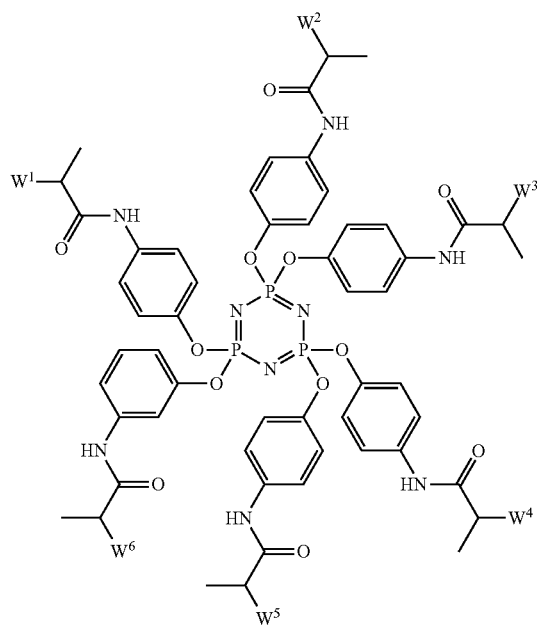

wherein each of $W^1$, $W^2$, $W^3$, $W^4$, $W^5$, and $W^6$ is independently a vinyl polymer.

2. The composition of claim 1, wherein the vinyl polymer comprises an acrylate monomer, an acrylamide monomer, a styrenic monomer, other vinylic monomer, or a combination thereof.

3. The composition of claim 1, wherein each of $W^1$, $W^2$, $W^3$, $W^4$, $W^5$, and $W^6$ is independently

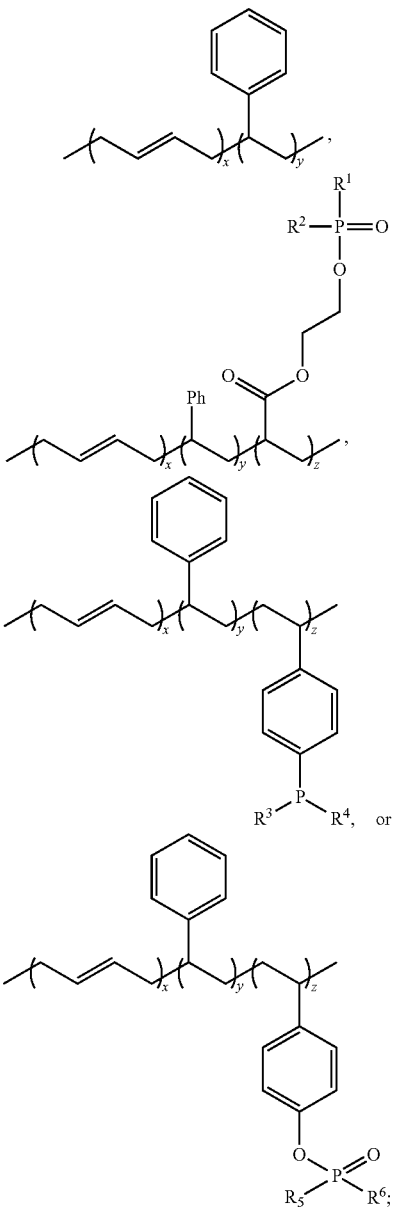

each of $R^1$, $R^2$, $R^3$, $R^4$, $R^5$, and $R^6$ is independently an unsubstituted hydrocarbyl, a substituted hydrocarbyl, an unsubstituted aryl, a substituted aryl, an unsubstituted alkoxy, a substituted alkoxy, an unsubstituted aryloxy, or a substituted aryloxy;

x is from about 1 to about 12,500;

y is from about 1 to about 12,500; and z is from about 1 to about 12,500.

4. The composition of claim 1, wherein the vinyl polymer is 1 to 40 wt % of the composition.

5. The composition of claim 1, further comprising a polymeric material.

6. The composition of claim 5, wherein the polymeric material includes a polylactic acid (PLA) homopolymer or a blend that includes a PLA polymer and a polycarbonate (PC) polymer.

7. A composition comprising: a phosphazene represented by formula wherein each of $W^1$, $W^2$, $W^3$, $W^4$, $W^5$, and $W^6$ is independently a vinyl polymer, the vinyl polymer comprising an acrylate monomer, an acrylamide monomer, a styrenic monomer, a vinylic monomer, or a combination thereof.

8. The composition of claim 7, wherein each of $W^1$, $W^2$, $W^3$, $W^4$, $W^5$, and $W^6$ is independently wherein:
each of $R^1$, $R^2$, $R^3$, $R^4$, $R^5$, and $R^6$ is independently an unsubstituted hydrocarbyl, a substituted hydrocarbyl, an unsubstituted aryl, a substituted aryl, an unsubstituted alkoxy, a substituted alkoxy, an unsubstituted aryloxy, or a substituted aryloxy;
x is from about 1 to about 12,500;
y is from about 1 to about 12,500; and
z is from about 1 to about 12,500.

9. The composition of claim 7, wherein the vinyl polymer is 1 to 40 wt % of the composition.

10. The composition of claim 7, further comprising a polymeric material.

11. The composition of claim 10, wherein the polymeric material includes a polylactic acid (PLA) homopolymer or a blend that includes a PLA polymer and a polycarbonate (PC) polymer.

12. A composition comprising: a phosphazene represented by formula wherein each of $W^1$, $W^2$, $W^3$, $W^4$, $W^5$, and $W^6$ is independently a vinyl polymer comprising:

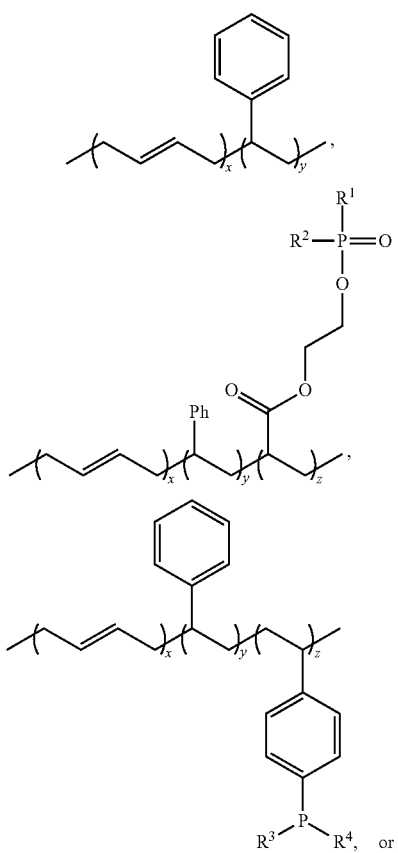

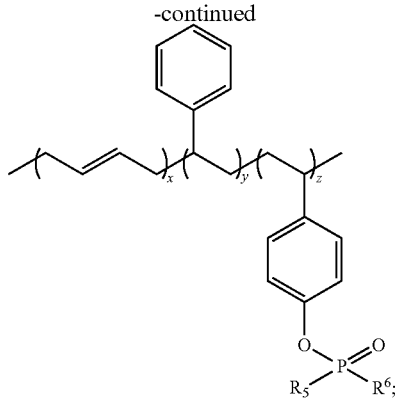

wherein each of $R^1$, $R^2$, $R^3$, $R^4$, $R^5$ and $R^6$ is independently an unsubstituted hydrocarbyl, and substituted hydrocarbyl, an unsubstituted aryl, a substituted aryl, an unsubsituted alkoxy, a substituted alkoxy, an unsubstituted aryl, or a substituted aryloxy, and x is from about 1 to about 12,500;
y is from about 1 to about 12,500;
z is from about 1 to about 12,500.

13. The composition of claim 12, wherein the vinyl polymer is 1 to 40 wt % of the composition.

14. The composition of claim 12, further comprising a polymeric material.

15. The composition of claim 14, wherein the polymeric material includes a polylactic acid (PLA) homopolymer or a blend that includes a PLA polymer and a polycarbonate (PC) polymer.

\* \* \* \* \*